United States Patent
Hirpara et al.

(10) Patent No.: US 8,062,363 B2
(45) Date of Patent: Nov. 22, 2011

(54) TENDON REPAIR APPARATUS AND METHOD

(75) Inventors: Kieran Hirpara, Doncaster (GB); Niall Quinn, Kilcolgen (IE)

(73) Assignees: Xircon Limited, Galway (IE); Kieran Hirpara, Doncaster (GB)

( * ) Notice: Subject to any disclaimer, the term of this patent is extended or adjusted under 35 U.S.C. 154(b) by 795 days.

(21) Appl. No.: 12/038,034

(22) Filed: Feb. 27, 2008

(65) Prior Publication Data

US 2009/0216326 A1 Aug. 27, 2009

(51) Int. Cl.
*A61F 2/08* (2006.01)
*A61B 17/06* (2006.01)
*A61B 17/04* (2006.01)

(52) U.S. Cl. .................. 623/13.14; 623/13.11; 606/222; 606/232

(58) Field of Classification Search .... 623/13.11–13.14, 623/13.2, 21.11, 21.15, 21.19; 606/139, 606/144, 148, 186, 151, 213, 224, 228, 232, 606/233, 236; 604/399
See application file for complete search history.

(56) References Cited

U.S. PATENT DOCUMENTS 4,469,101 A * 9/1984 Coleman et al. ............... 606/151
6,613,059 B2 * 9/2003 Schaller et al. ............... 606/157
2004/0088003 A1 * 5/2004 Leung et al. .................. 606/228
2006/0161160 A1 * 7/2006 Sander et al. ................... 606/72

OTHER PUBLICATIONS

L. Gordon et al., Flexor Tendon Repair Using a Stainless Steel Internal Anchor, Journal of Hand Surgery, pp. 37-40, vol. 23B, No. 1, Feb. 1998.
McKenzie et al., An Experimental Multple Barbed Suture for the Long Flexor Tendons of the Palm and Fingers, J. of Bone and Joint Surgery, pp. 440-447, vol. 49B, No. 3, Aug. 1967.
P.C. Shaw, A Method of Flexor Tenson Suture, Journal of Bone and Joint Surgery, pp. 578-587, vol. 50B, No. 3, Aug. 1968.

* cited by examiner

*Primary Examiner* — Thomas J Sweet
*Assistant Examiner* — Yashita Sharma
(74) *Attorney, Agent, or Firm* — Schiff Hardin LLP (57) ABSTRACT

A method and apparatus for tendon repair includes an elongated member of a generally tubular shape having two barbed sections with oppositely directed barbs and a middle portion between the barbed sections. The barbs are cut from the tubular body leaving a mesh-like body of interconnected struts. The middle portion is also formed of interconnected struts. A needle and suture is connected at both opposite ends of the elongated member and used to pull the barbed sections into respective ends of a severed tendon. The barbs bite into the tendon tissue to hold the ends together. The sutures are preferably cut off at the tendon surface at a location spaced from the rejoined ends. One or more of the tendon repair devices may be used to repair each tendon, optionally with perimeter stitching at the rejoined ends.

19 Claims, 11 Drawing Sheets

TENDON REPAIR APPARATUS AND METHOD

BACKGROUND OF THE INVENTION

1. Field of the Invention

The present invention relates generally to an apparatus and method for repair of tendons and in particular to an elongated apparatus having barbs for insertion into a severed tendon to secure the ends of the severed tendon to one another.

2. Description of the Related Art

Tendons are tough cords or bands of dense white fibrous connective tissue that unite a muscle with some other part of the body (such as a bone) and transmit the force which the muscle exerts to that body part. In general, a tendon is designed to transmit force of a muscle to a bone across a joint. The main constituent of a tendon is type I collagen, although other types of collagen as well as other materials are present in small quantities. Long strands of collagen protein, known as fibrils are bundled with tenocytes into fascicles, which are held together with the endotenon, a loose connective tissue, to form fiber bundles that are collected to form the tendon. Tendons may become damaged and require repair or they may be severed such as by an injury and must be reconnected. Tenorrhaphy is the surgical suture of the divided ends of the tendon, sometimes called tendinosuture or tenosuture.

Much of the tenorrhaphy literature focuses on increasing the tensile strength of the repaired tendon in order to decrease the tendon rupture rate associated with early mobilization of the effected body part. Early mobilization is important to avoid adhesion of the healing tendon to the surrounding tissue by strands of scar tissue. Various techniques of suturing the ends of the tendon together have been proposed, these involving different configurations of suture threading through the tendon and between the severed ends. The techniques include core suturing and peripheral suturing. Multiple strands of suture material extend between the tendon ends in these proposals. Some literature suggests decreasing the number of strands bridging the repair site in order to minimize soft tissue dissection, decrease the operative time and limit handling of the injured tendon. It is still important to repair a tendon with sufficient strength to allow early mobilization, but the achievement of strength at all costs is no longer considered essential. A current preferred method of flexor tendon repair is a four strand technique using four suture strands extending between the ends of the tendon. This number of strands achieves sufficient strength to allow early passive or light active mobilization, however four strand repairs remain relatively complex.

There is a desire to provide a tendon repair that is less complex to perform, reduces handling of the tendon, reduces surface roughness of the repaired tendon, and enables early mobilization of the affected body part.

SUMMARY OF THE INVENTION

The present invention provides an apparatus for repair of tendons, the apparatus having an elongated body with a suture or strand extending from each opposite end of the elongated body. A needle may be connected to each suture by which the suture and then a portion of the elongated body is drawn into the tendon. Barbs are provided on at least portions of the elongated body to bite into the tendon and prevent easy withdrawal of the apparatus from the tendon. The barbs at different portions of the apparatus are oriented in opposite directions to enable relatively easy insertion of the apparatus into the ends of the tendon yet resist withdrawal. When the opposite ends of the apparatus are inserted into opposing ends of the severed tendon, the apparatus holds the two sections of the tendon and may be used to rejoin the severed tendon ends together. The apparatus provides sufficient holding strength to enable early mobilization of the tendon.

In preferred embodiments, the elongated body of the apparatus includes an elongated tube-shaped body that is formed of an open mesh or framework of interconnected struts. At a first end of the elongated body is a connection to a suture. Adjacent the first end is a first barbed portion, then a middle portion, a second barbed portion and finally a second end connected to another suture. The barbs of the first and second barbed portions are directed toward one another and extend outward from the tube-shaped mesh or framework body. The middle portion of the tube-shaped mesh or framework body lacks barbs. The mesh framework apparatus is formed of a flexible and strong material and thus enables the repaired tendon to be mobilized shortly after the repair while permitting flexing of the repaired tendon without rupture, or separation, of the severed tendon ends from one another.

An alternative embodiment includes barbed sections joined by a flexible section that need not have a lattice structure but may have some other flexible construction. The flexible section reduces interference with flexing of the repaired tendon. Alternative flexible middle sections can include but are not limited to a flexible rod, flexible tube, a cable, jointed members, a spring member, a cord or stranded member, monofilament member, section of suture material, or other flexible portion.

Another alternative is a tendon repair device that has a single barbed section for insertion into a tendon and a fastening means at the other end for connection to a bone or other body portion. Various known bone anchoring means and methods may be used to connect to the bone. A tendon can thereby be anchored to a bone, for example, if the injury has caused the tendon to be severed at or very near the bone. This embodiment is essentially half of the two sided device described herein, a single ended device.

A method of tendon repair is also provided, as well as a method for forming a tendon repair apparatus. Various alternative embodiments of the apparatus and method are disclosed, some of which provide the apparatus formed of a metal and others formed of a biodegradable polymer or other material. Medically active agents may be provided in or on the apparatus.

DETAILED DESCRIPTION OF THE PREFERRED EMBODIMENTS

Figure 1:
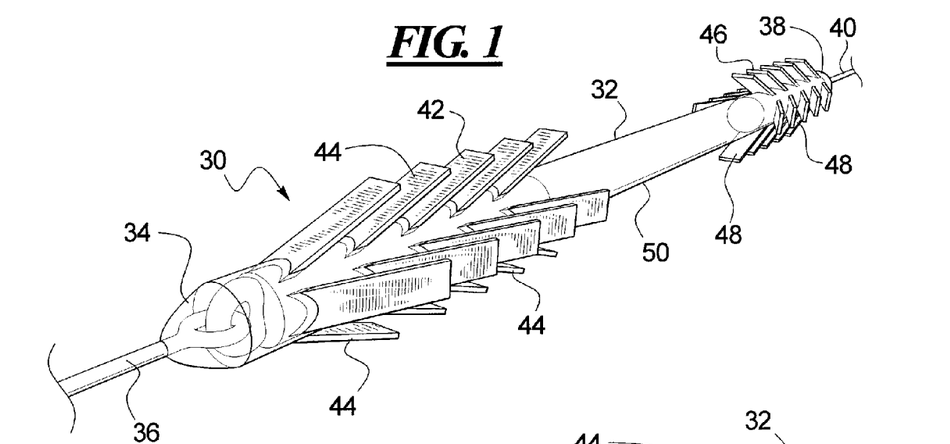
FIG. 1 is an end perspective view of a tendon repair apparatus.

Referring first to FIG. 1, an early embodiment of a tendon repair apparatus 30 is shown. The tendon repair apparatus 30 includes an elongated body 32 that has a first end 34 connected to a suture 36. A second opposite end 38 is connected to a second suture 40. A short distance from the first end 34 is a first barbed portion 42 that includes a number of barbs 44 in an arrangement around the elongated body. A short distance from the second end 38 is a second barbed portion 46 that includes an arrangement of barbs 48 around the elongated body. Between the two barbed portions 44 and 46 is a middle portion 50 that has no barbs. The barbs of the first barbed portion 44 and the barbs of the second barbed portion 46 are directed toward the middle portion 50.

Figure 2:
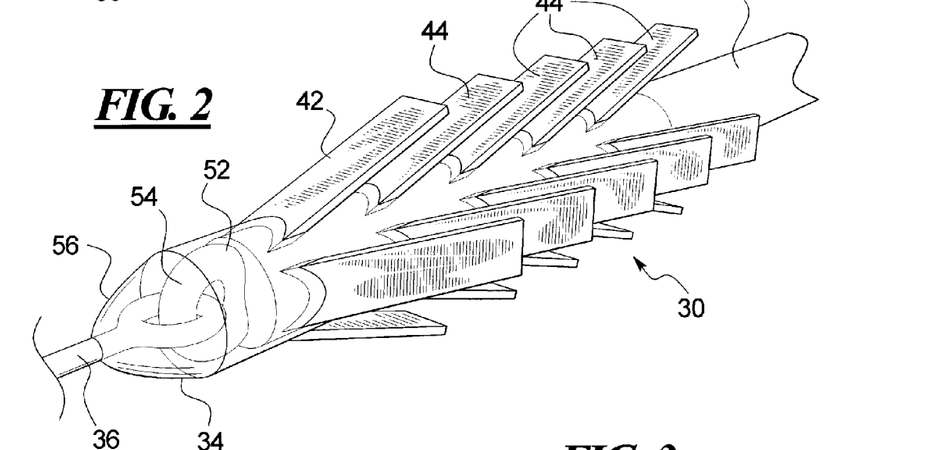
FIG. 2 is an enlarged view of one end of the tendon repair apparatus of FIG. 1.

An enlarged view of an end of the tendon repair apparatus 30 is shown in FIG. 2. The suture 36 is connected at the end 34 by a suture connection 52. The suture connection 52 of the illustrated embodiment includes a loop element 54 fastened into the elongated member with the suture 36 fastened to the loop element 54. The loop element 54 and the attachment to the suture are encased in a biocompatible material 56, such as a material that serves as a filler, to provide a smooth transition from the suture 36 to the body of the elongated member so that pulling the elongated member into the tendon behind the suture is easier.

Also in FIG. 2, the barbs 44 of the barbed portion 42 extend outward from the body of the elongated member at an angle, which for this embodiment is a uniform angle for all barbs. The barbs 44 extend outward equally in all directions from the device and in the illustrated embodiment are provided in four columns.

Figure 3:
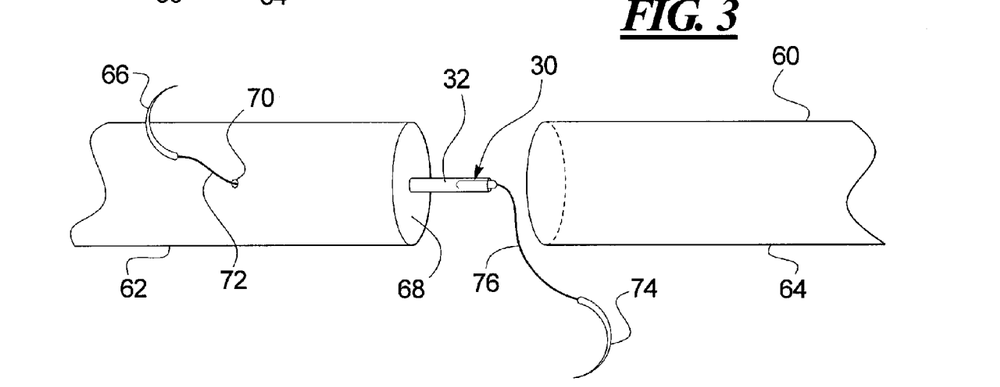
FIG. 3 is a schematic diagram showing a step in a repair of a severed tendon using the apparatus of FIG. 1.

To repair a severed tendon, which is shown schematically at 60 in FIG. 3, end faces of the two tendon sections 62 and 64 are to be rejoined. In FIG. 3, a repair is underway using the present device in which a needle 66 has been inserted into an end face 68 of the first part 62 so as to run along the axial length of the tendon 60 for a distance and then is directed to emerge from the side wall of the tendon at a location 70 spaced from the end face 68. The needle 66 has a suture 72 connected to it that is drawn along behind the needle into the tendon 60 so that a portion of the suture 72 extends out of the side wall of the tendon 60 at the location 70. The needle and/or suture may be grasped by a needle gripper to assist the medical professional in moving the needle and suture through the tendon. The needle 66 and suture 72 are further drawn into the tendon 60 to pull the end 34 and first barbed portion 42 of the elongated body 32 into the tendon. Pulling or drawing in of the elongated body 32 is halted when the first barbed portion 42 is entirely in the tendon. A part of the middle portion 50 generally extends from the end face 68.

Preferably, half of the elongated body 32 is in the first portion 62 of the tendon 60 and the other half extends from the end face 68. To ensure that half of the elongated body 32 remains in the tendon and does not emerge from the tendon at the location 70, the needle 66 must exit the tendon surface only at a distance greater than half the length of the elongated body 32 from the end face 68. FIG. 3 shows a second needle 74 and second suture 76 extending from the second end of the elongated body 32 for insertion into the second portion 64 of the tendon.

Figure 4:
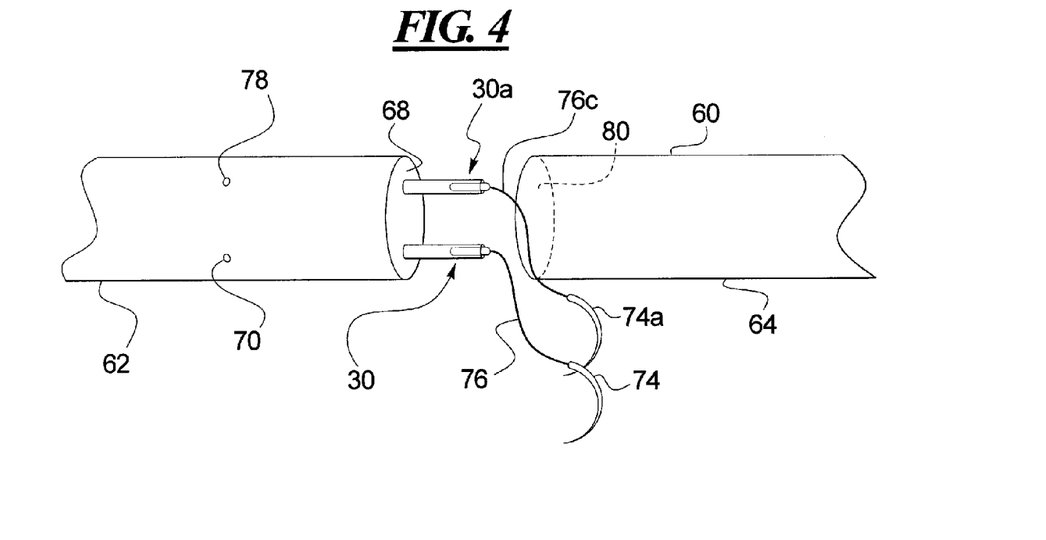
FIG. 4 is a further step in the repair of a severed tendon that follows the step illustrated in FIG. 3.

FIG. 4 shows a further step in the repair process, wherein the first suture and first needle have been trimmed off at the location 70 where they emerge from the tendon side wall. A second device 30a has been inserted into the first portion 62 of the tendon 60. The second device 30a is substantially identical to the first device 30 that was used in FIG. 3 and is also inserted so that about half of the elongated body is in the tendon and half is extending out. The suture and needle have also been trimmed off of the second device 30a at a location 78 where it emerges from the side wall. The suture is preferably cut as close to the side wall of the tendon as reasonably possible so that little or no suture material projects from the side of the tendon. A smooth outer surface of the repaired tendon is thereby provided. FIG. 4 shows the second needle 74a and suture 76a extending from the end of the second device 30a along with the needle 74 and suture 76 of the first device from FIG. 3.

FIG. 4 shows a repair using two of the tendon repair devices. It is also possible to repair the tendon using a single device, three devices, four devices, or more. This depends in part on the relative sizes of the devices and the tendon being repaired. The devices are shown inserted in parallel to one another and along the axis of the tendon. It may be desirable in some instances to angle the devices to one another and/or to the axis of the tendon.

Figure 5:
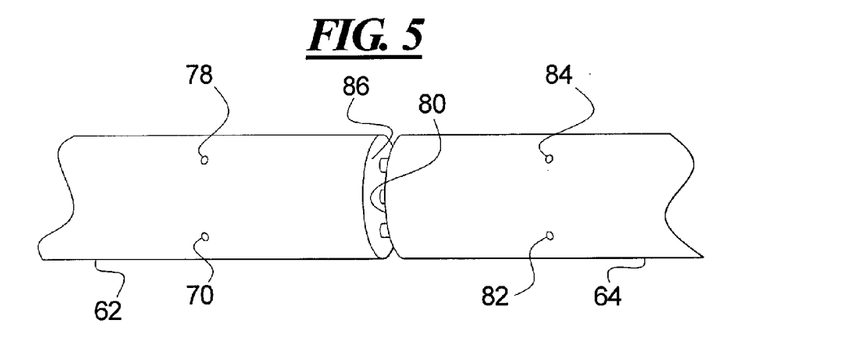
FIG. 5 is yet a further step in the repair of the severed tendon.

In a further step, the second needles 74 and 74a are inserted into an end face 80 of the second portion 64 of the tendon. The needles 74 and 74a are pushed into the tendon and along the axis and then out of the side wall of the tendon at locations spaced from the end face 80 by at least half the length of the elongated body 32. The sutures 76 and 76a are pulled through the tendon 60 until the second barbed portion 46 of elongated body is in the tendon. As shown in FIG. 5, once the two devices 30 and 30a have been pulled into the second portion 64, the sutures and needles are cut off at the emergence locations 82 and 84. There is no need to knot the sutures at the side walls or otherwise secure the sutures since it is the barbs of the elongated device that secure the tendon portions 62 and 64 together, not the sutures. This enables a repair of a tendon while maintaining a smooth outside surface of the tendon, which is beneficial for healing and for unrestricted use by the patient.

The end faces 68 and 80 are spaced apart from one another by a short distance in FIG. 5. It is desirable for the more rapid healing that the ends be in contact with one another, so the medical professional preferably pushes the tendon parts together to enable the barbs to bite into the tendon tissue so as to hold the end faces in contact with one another. The devices 30 and 30a thereby secure the tendon together at the core.

Figure 6:
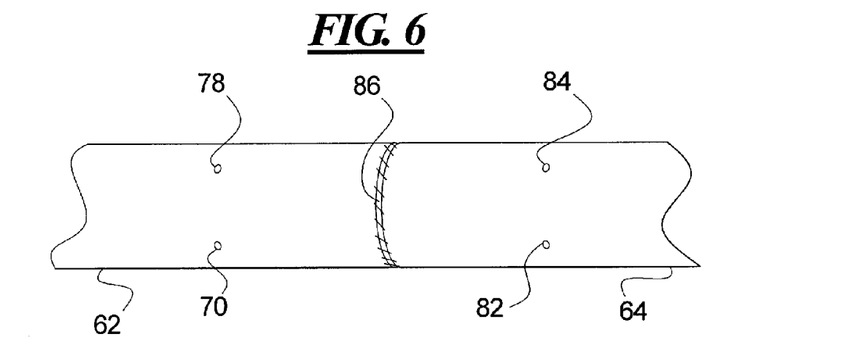
FIG. 6 is a final step in the repair of the severed tendon.

It may be desirable to secure the perimeter of the tendon together as well, as this leads to a smoother surface and reduces the chance of snagging at the healing site. As such, one preferred method for tendon repair secures the perimeter of the tendon end faces together by peripheral suture stitches 86, as shown in FIG. 6. A tendon repaired in this matter should be durable enough for early mobilization therefore favoring intrinsic healing over extrinsic healing. The peripheral stitch 86 smoothes the tendon surface and increases the repair strength, although this may not be necessary in every instance.

Figure 7:
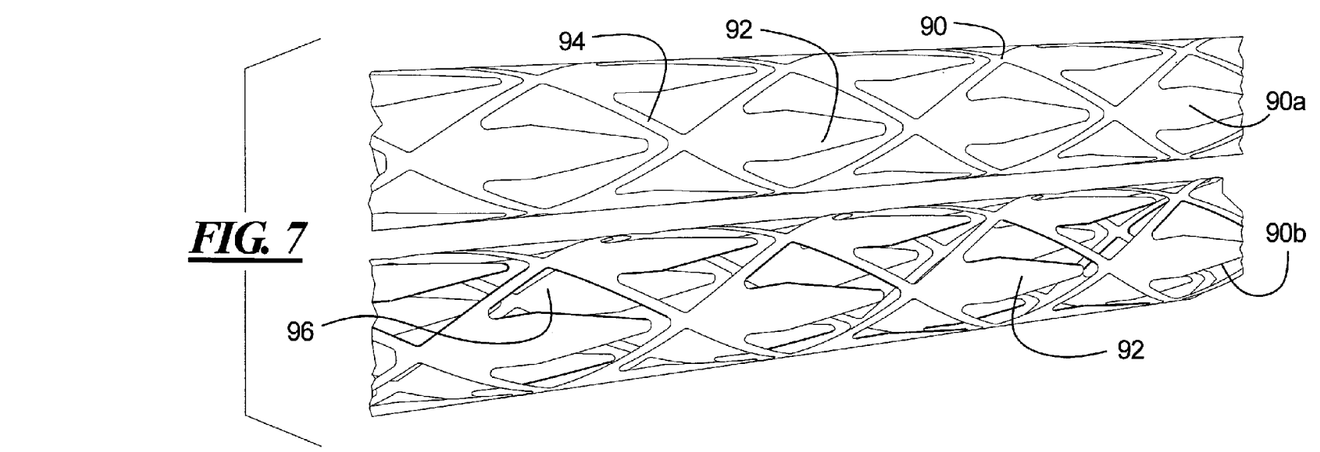
FIG. 7 is a photograph of a first preferred embodiment of the apparatus for tendon repair, showing a first tube etched for laser cutting and a second tube that has been cut.

The tendon repair method shown and described in the foregoing may use any of several preferred embodiments of the tendon repair device. A first preferred embodiment as shown in FIG. 7 was developed following work on the embodiment of FIG. 1. In FIG. 7, a tube 90 of the desired diameter of the elongated body is provided. In a preferred embodiment, the tube is of nitinol, an alloy at least primarily of nickel and titanium, which is a flexible, strong material that is also has super elasticity at body temperature and is biocompatible. Other materials may be used instead for the present device including various steel alloys or other metals. It is also contemplated to form the device of a material other than metal, including a polymer or a polymer/metal composite. In an advantageous embodiment, the device is formed of a biodegradable material, such as a polymer, that is resorbed into the body. The further advantages may be achieved if the material of the device is coated or impregnated with biologically active agents, growth hormones or other agents or materials.

The illustrated nitinol tube 90 is provided with barbs 92 by cutting the tube to form barbs from the tube material. The cutting is performed by a laser that cuts a pattern 94 in the tube 90. Instead of laser cutting, other techniques for cutting of the tube may be used as desired. Two tubes are shown in FIG. 7, the tube 90a has been cut with the desired pattern and the tube 90b has had the excess material removed yet retains the tube shape. The removal of the excess material forms openings 96 in the tube 90 around the barbs 92. In the illustrated embodiment, the openings 96 are diamond shaped, with a barb 92 extending from an apex of the diamond into the opening to the opposing corner of the diamond. The diamond shaped openings 96 are arranged shifted by half a length of the opening in alternating rows to form a diagonal mesh of interconnected struts 98. The struts 98 of the mesh wrapped in a spirals in opposite directions along the length of the barbed portion of the elongate device. The mesh retains the structure of the tube 90 at the barbed portion.

The barbs 92 themselves are shaped with a taper from a pointed free end to a wider base at the connection to the mesh or struts. The barbs 92 may be of a length extending the full length of the diamond shaped openings 96 or may be shorter. The barbs 92 may be a mix of longer and shorter barbs on the barbed portion in any desired arrangement, or they may all be of the same length. The pointed free end of the barbs 92 may be sharply pointed or provided with a more rounded tip, and the barbs may be of various widths. The barbs 92 are bent outward at or near the junction to the struts 98 to extend at an angle from the body of the device. The bending of the barbs 92 is performed by lifting the barbs sufficiently to overcome any shape memory the material has so that the barbs are raised out of the tube shape. This may require bending the barbs beyond the desired final angle so that the barbs achieve the desired angle when released. The barbs may be formed or positioned in other ways, such as by being molded in position or otherwise positioned as will be understood by those of skill in the art. The barbs of the embodiment of FIG. 7 are offset from one another from row to row. In one embodiment, 24 barbs are provided at each barbed portion of the device.

The illustration of FIG. 7 shows only one of the barbed portions of the device. The other barbed portion is also cut with the same pattern to form barbs, but with the pattern flipped end-for-end so that the barbs are directed in the opposite direction. At the ends of the elongated embodiment, the tube remains uncut to enable the suture to be inserted into the tube and fastened there, such as by crimping or adhesive. It is also foreseen that some cutting or shaping of the tube may be provided at the end to enable a different fastening of the suture in the tube or a more secure fastening, such as by forming teeth in the tube to engage the suture. The middle portion of the elongated member may be left uncut but in a preferred embodiment is cut with a pattern to form openings such as diamond shaped openings as well. The openings of the middle portion lack the barbs and result in an arrangement of struts that provide flexibility to the middle portion. Other patterns of openings for the middle portion may be provided as well.

Figure 8:
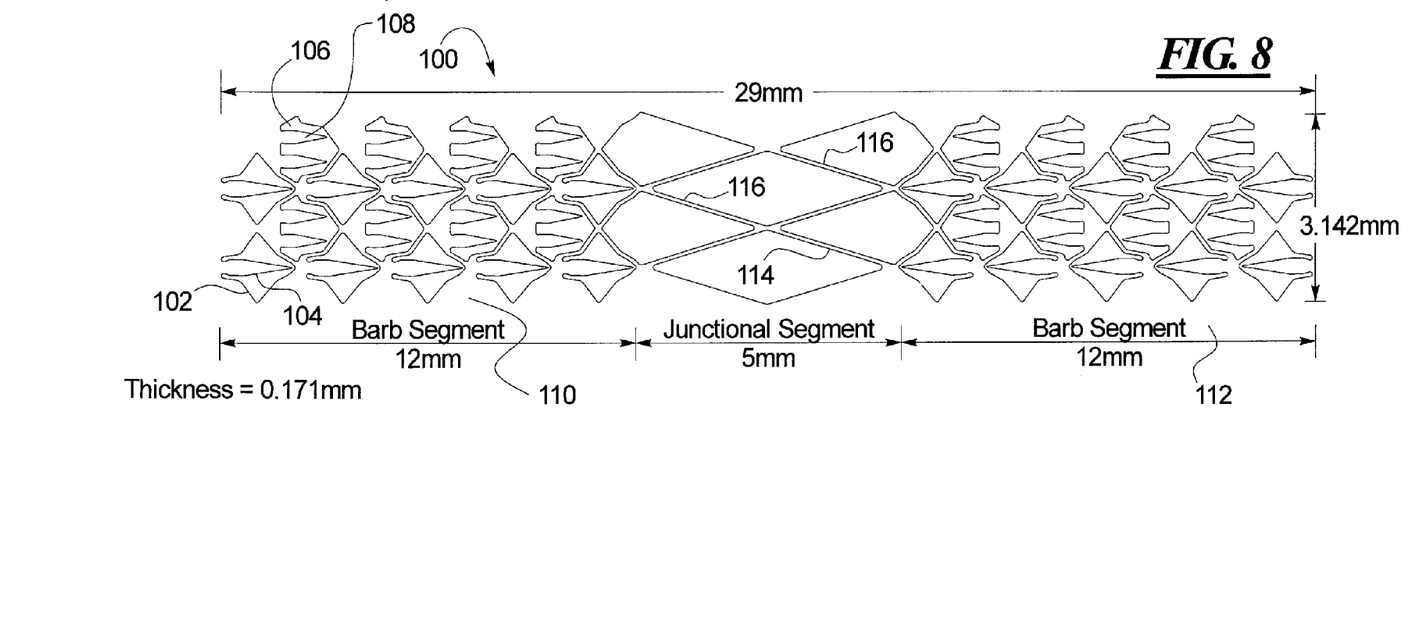
FIG. 8 is a diagram of the vector path for a cutting tool to cut a tube to form a tendon repair apparatus that varies somewhat from that shown in FIG. 7.

To generate the cut tube, particularly with a cutting laser, a pattern is formed that is wrapped around the laser in the course of the cutting step. The pattern or profile is a vector path for the cutting tool that is followed under computer control. Care must be taken when wrapping the vector cutting path around the tube to avoid misalignments that might lead to notches or other weak points in the device. In FIG. 8 is shown one such vector path 100 for laser cutting a tube to form an embodiment which differs somewhat from that shown in FIG. 7. When wrapped around a tube, the vector path 100 forms two barbed portions 110 and 112 with oppositely directed barbs and a middle portion 114 therebetween. The barbed portions 110 include in alternate columns a sequence of generally diamond shaped openings 102 with long barbs 104 extending diagonally across the openings 102 when formed. The alternate columns include a sequence of generally diamond shaped openings 106 each with two smaller, shorter barbs 108 in a side-by-side arrangement. In each barbed portion, two columns of each type of barb are provided with five long barbs 104 in each column and four pairs of short barbs 108 in each column. The openings 102 and 106 have a shape the varies from a diamond shape in order to accommodate the different barbs of the two columns. In particular, the sides of the single barb openings 102 curve inwardly while the sides of the two barb openings 106 curve outwardly. The two barbed sections 110 and 112 are symmetrical to one another.

The middle portion 114 between the two barbed sections 110 and 112 has been cut to form elongated diamond shaped openings that leave cross struts 116 extending across the middle of the device. The cross struts 116 provide sufficient strength to prevent separation of the barbed portions 114 and 116 from one another under the tension exerted by the tendon and so bridge the repair while preventing rupture of the repaired tendon. The arrangement of struts that make up the barbed portion and the middle portion provide flexibility to the device. But perhaps as important is that the strut arrangement provide elasticity in the length direction of the device so as to accommodate the viscoelastic response, or lengthening and shortening, of the tendon during use. Preferably, the arrangement of struts and other structural elements, the dimension of those elements, the material of which they are formed, the annealed or heat affected state of those elements, and perhaps other factors are provided to substantially match the longitudinal elasticity of the device to the longitudinal elasticity of the tendon. It may be desired in some instances to provide less elasticity of the tendon repair device than of the uninjured tendon.

The dimensions of the vector path 100 are matched to the dimensions of the resulting device, and these may be changed depending on the size of device desired, both in terms of the diameter of the tube being used to form the device and the length of the resulting device. The dimensions of FIG. 8 are but one example of a wide variety of possible dimensions. It is envisioned to change the dimensions of the device depending on the size and shape of the tendon to be repaired.

Figure 9:
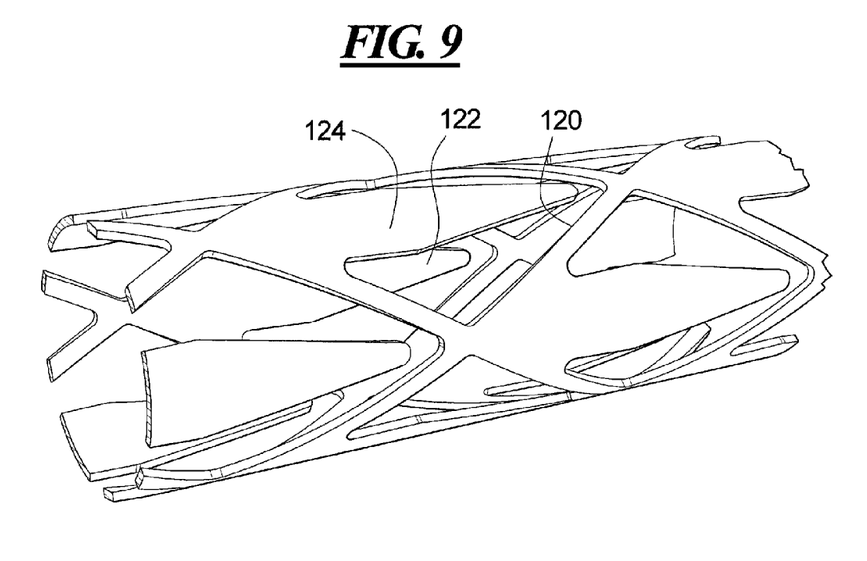
FIG. 9 is a photograph of the present apparatus of the first preferred embodiment of the elongate member for tendon repair after cutting the tube and with the barbs still in the tube shape.

FIG. 9 is a photograph of a section of barbed portion of an embodiment of the tendon repair device. The initial tube has been cut, such as by laser cutting, to form a crossed arrangement of struts 120 defining openings 122 in each of which are barbs 124. The embodiment of FIG. 9 has a single barb 124 in each opening 122. At the stage of manufacture shown in FIG. 9 the device still retains it's tube shape.

Figure 10:
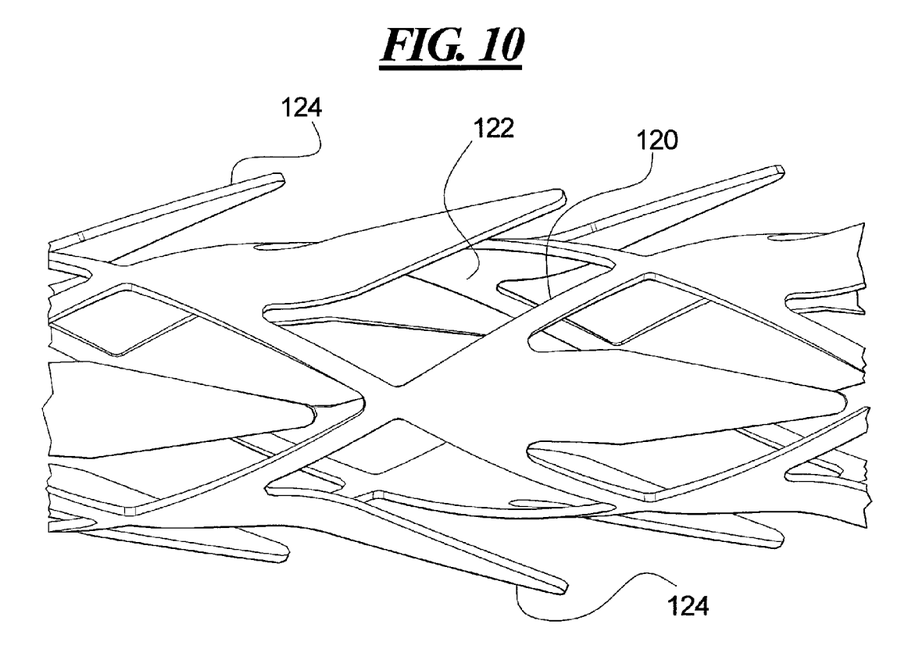
FIG. 10 is a photograph of the first preferred embodiment of the elongated member with the barbs raised at an angle.

In FIG. 10, the barbs 124 have been bent outward at an angle to the device. The barbs 124 preferably extend at a relatively shallow angle so as to engage into the tissue of the tendon while being prevented from being bent over backwards. To achieve the shallow angle outward bend of the barbs 124 with a shape-memory material such as Nitinol, it was necessary to bend the barbs outward to approximately 180 degrees so that a bend was retained by the barbs when released from the bending force. Other ways of positioning the barbs are also within the scope of this invention, such as forming the barbs already in the outwardly angled position, by molding the barbs in position, by heat treating the barbs so that they bend or so that they retain a bend, or by other forming methods as are known. The engagement of the barbs into the tendon material resists separation of the previously severed tendon portions, enabling mobilization without rupture.

The angle of the barbs may vary from barb to barb or from row to row or column to column or by any other arrangement. Other arrangements of barbs on only some sides or sections of the device or in other numbers of columns or even not in columns are possible. The length of the barbs is uniform in some embodiments; the barbs may be of unequal lengths in other embodiments. The shape of each barb may vary from device to device or even at different parts of one device.

Figure 11:
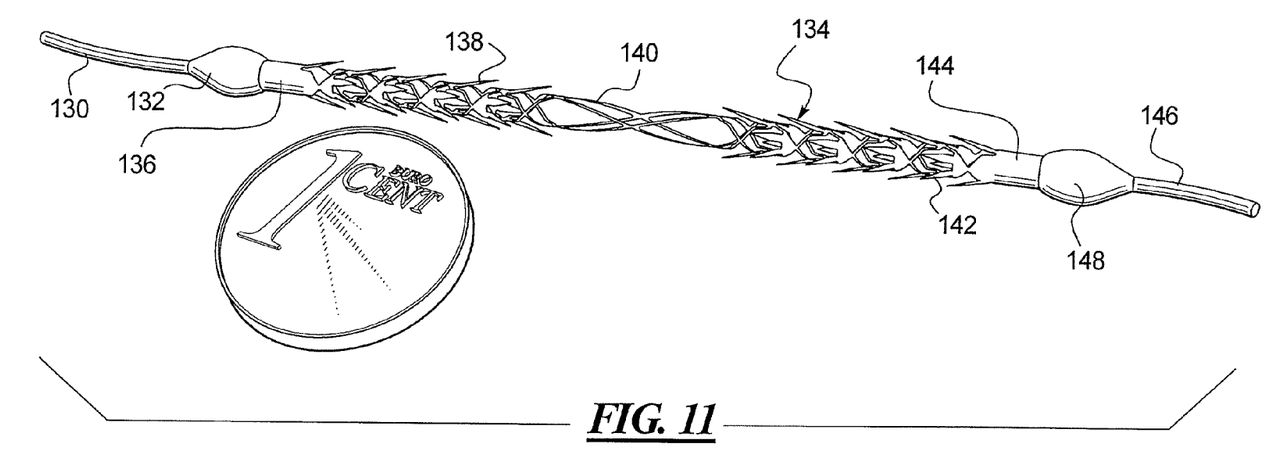
FIG. 11 is a photograph of the first preferred embodiment of the elongated member with sutures connected at each end.

Turning now to FIG. 11, a tendon repair device formed according to the foregoing description is shown adjacent a coin for reference. A suture 130 is connected to one end 132 of the elongated member 134, where a taper is formed by a material that eases the entry of the elongated member into the tendon when pulled behind the suture. The taper may be formed of a filler material and it may be desirable that the filler material can also serve as an adhesive to affix the suture 130 and elongated member 134 together. A tubular end portion 136 of the elongated member 134 provides a surface for adhesive bonding to the suture 130, wherein the suture extends a short distance into the tube at the end portion 136. The end portion 136 connects to a first barbed portion 138. The first barbed portion 138 includes long barbs and paired short barbs according to the vector cutting path of FIG. 8. A middle portion 140 of elongated struts extends across the middle of the device. A second barbed portion 142 connects from the middle portion 140 to the uncut tube of the second end portion 144, into which extends an end of a second suture 146, where the taper 148 of adhesive filler material, in this instance, secures the suture.

The sutures 130 and 146 have a smaller diameter than the elongated member 134, particularly when subject to tension, which ensures that the tunnel in the tendon formed by pulling the suture through the tendon is smaller than the diameter of the elongated member. A snugger fit and better engagement of the elongated member in the tendon is thereby ensured. The suture may also be the same diameter as the elongated member in some embodiments. The suture material may be any known suture material, including multi-stranded suture material, monofilament suture material, biodegradable material or permanent suture material.

As can be seen in the foregoing illustrations, the open mesh design, or latticework, of the preferred tendon repair device provides space for healing of the tendon and minimizes interference with vascularity of the healing and healed tendon. As noted above, this also provides elasticity and flexibility to the device to reduce interference with use of the repaired tendon. Alternative embodiments of the present device replace the latticework middle portion with some other structure, material or device to provide flexibility.

Many alternative connections between the suture and the body of the elongated member are also possible. For example, the suture may extend into the hollow end of the elongated member and be held there by some fastening means or method. For example, the suture may be held in the end of the device by an adhesive that can also be formed into a taper to provide a smooth transition between the suture and the elongated member. The adhesive and taper material may be two separate materials that are applied in separate steps. Another alternative is to hold the suture in the hollow body of the device by crimping the hollow device onto the suture (where the material of the tube readily permits such crimping) or a combination of crimping and adhesive. A roughened or toothed inner surface may be provided on the tube section to grip the suture. A further alternative is to provide the suture material extending through the entire length of the elongated body or to shape the suture material to form the taper that permits the elongated member to be pulled into the tendon. Other fastening means and methods are also possible.

Figure 11A:
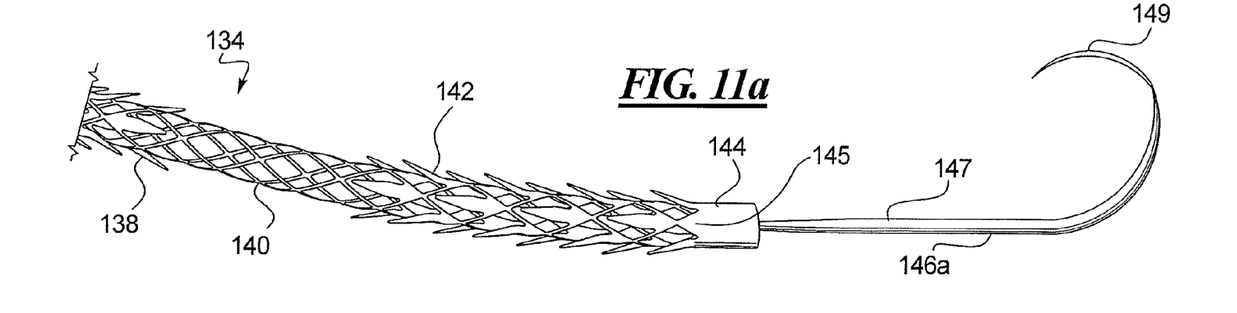
FIG. 11a is a schematic representation of an embodiment of the tendon repair device with a removable suture.

An alternative embodiment provides a disengageable connection between the suture 145 and the elongated member 134 is shown in FIG. 11a. Only a portion of the elongated member 134 is shown, including the second end 144. The end 144 includes an eye or other opening 145 (which is inside the end of the end portion 144) through which the suture 146a is fed. The suture 146a includes an elongated loop 147 of the suture material that may extend all the way to the needle 149 as shown or may be rejoined to the suture material at a position spaced from the end portion 144. The loop 147 is sufficiently elongated to extend from the tendon at the opening in the tendon side wall. After the elongated member 134 is in place in the tendon, one side of the loop 147 is cut and the suture 146a removed from the tendon by being pulled through the eye 145. In this way, the suture 146a is removed from the tendon altogether, so no suture extends to the side wall of the tendon to interfere with healing. The removable suture may be provided on one or both ends of the device. Other methods for selectively removing the suture from the device may be provided instead and are encompassed within the scope of this invention.

The disengageable suture permits a minimally invasive repair of the tendon. The ends of the ruptured tendon are exposed only in a small area and without the need for opening the tendon sheath or other surrounding soft tissues on either side of the exposed ends. The needle pulling the suture material is passed through the interior of the tendon then through the tendon sidewall at the suture exit location, as shown above. The needle is then directed through the tendon sheath and possibly through other tissues of the patient, including out through the skin. The suture pulls the device into place in the tendon and then the loop of suture material is cut and removed. The device remains in the tendon to repair the rupture and aside from the opening at the tendon rupture site only small needle holes are present through the skin and other tissues. Without the need to expose the tendon along its length, less work is required to close the surgery site, shortening the procedure considerably. This lessens the time that the patient is under anesthesia, and reduces work for the surgeon. Faster healing, less risk of infection, and faster recovery and return to use of the effected body part are provided.

Figure 12:
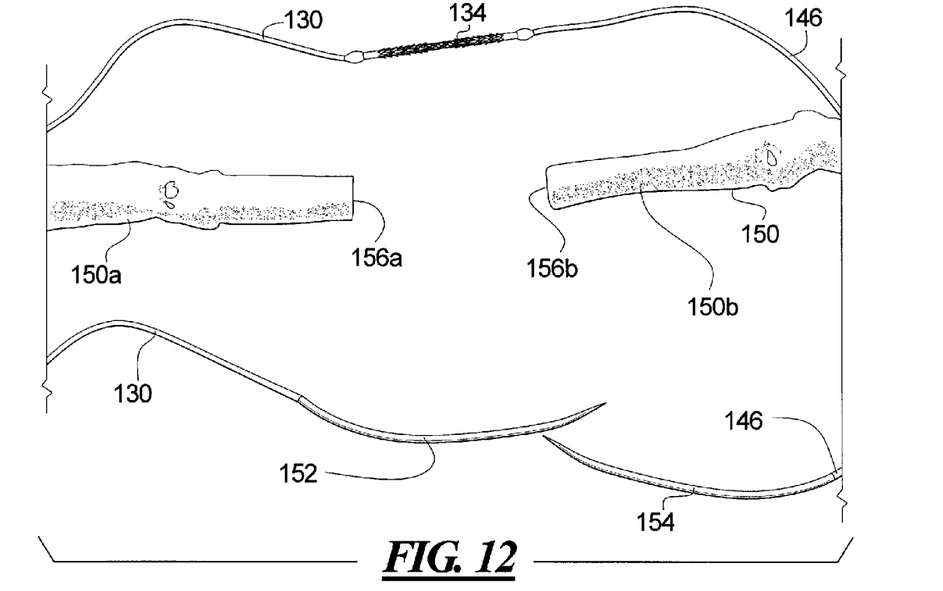
FIG. 12 is a photograph of a severed tendon to be repaired and the first preferred embodiment of the present device provided with sutures and needles.

FIG. 12 shows the complete tendon repair device ready to repair a severed tendon 150. FIGS. 12-16 shows a tendon 150 that has been removed from a pig and has been severed into a first part 150a and a second part 150b. The pig tendon 150 is a good model of a human tendon for purposes of illustrating the steps for repair of a lacerated tendon. In practice, the tendon being repaired would be that of a human patient and the repair would be carried out by exposing the ends of the ruptured tendon and performing the repair through a surgical opening in the patient's tissues. The present apparatus and method has particular utility in repair of tendons of the human hand. It is also possible that the present device may be used for a tendon repair on a non-human animal.

The tendon 150 of FIG. 12 a porcine flexor tendon which undergoes flexion, or bending during use. The tendon 150 has been severed into two parts, a first part 150a and a second part 150b. The tendon repair device substantially similar to the device as shown in FIG. 11 is provided for repair of the tendon 150. The tendon repair device includes the elongated member 134 to one of which is connected the suture 130 and to the other end of which is connected the suture 146. The sutures 130 and 146 extend out of the field of view and back in to show elongated curved needles 152 and 154 that are connected to the sutures 130 and 146, respectively, at the ends opposite the elongated member 134. The needles 152 and 154 are each longer than the elongated member 134 in the illustration. The needles should at least be longer than half the elongated member to ensure that the suture may be brought out of the side wall of the tendon at a location spaced from the end faces 156a and 156b of the tendon by a length greater than half the length of the elongated member. Use of elongated needles is desired; and the needles may be straight or curved, depending on user preference. In one embodiment, the needles are affixed to the suture material and in another embodiment the suture material is threaded through an eye of the needle. Which of these attachments is used may depend on whether a thicker or thinner suture material is used or on user preference. Other types of connection between the needle and suture are also possible.

Figure 13:
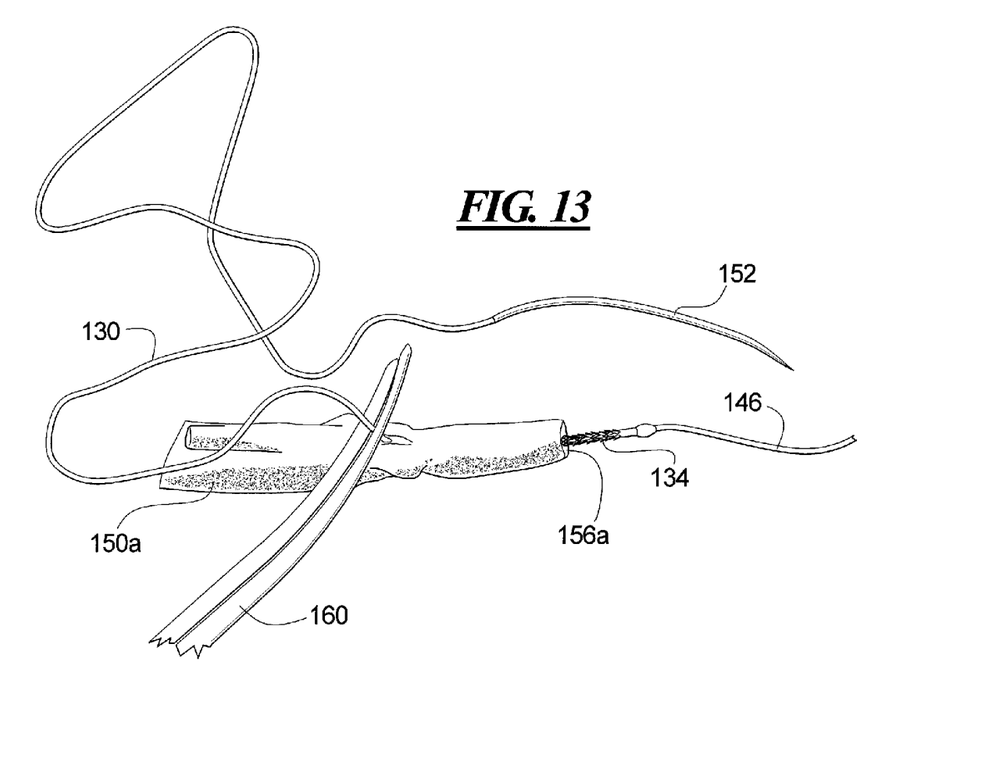
FIG. 13 is a photograph of the first preferred embodiment of the tendon repair apparatus with its first end pulled into a first portion of the severed tendon by a first suture.

In FIG. 13, the first portion 150a of the tendon 150 is being engaged first. The needle 152 has been inserted into the end face 156a and directed generally axially along the tendon to a point beyond half the length of the elongated member 134, where it is directed out of the side wall of the tendon. The needle 152 is pushed and then pulled through the tendon to draw the suture 130 through the tendon portion 150a and out of an exit location 158a. A needle holder may be used if desired by the medical professional. The suture 130 is further pulled to pull the elongated member 134 into the tendon portion 150a at least sufficiently that the first barbed portion 138 is inside the tendon portion 150a. The second half of the elongated member 134 extends from the end face 156a. A scissors 160 is shown cutting the suture 130 in the illustration.

Figure 14:
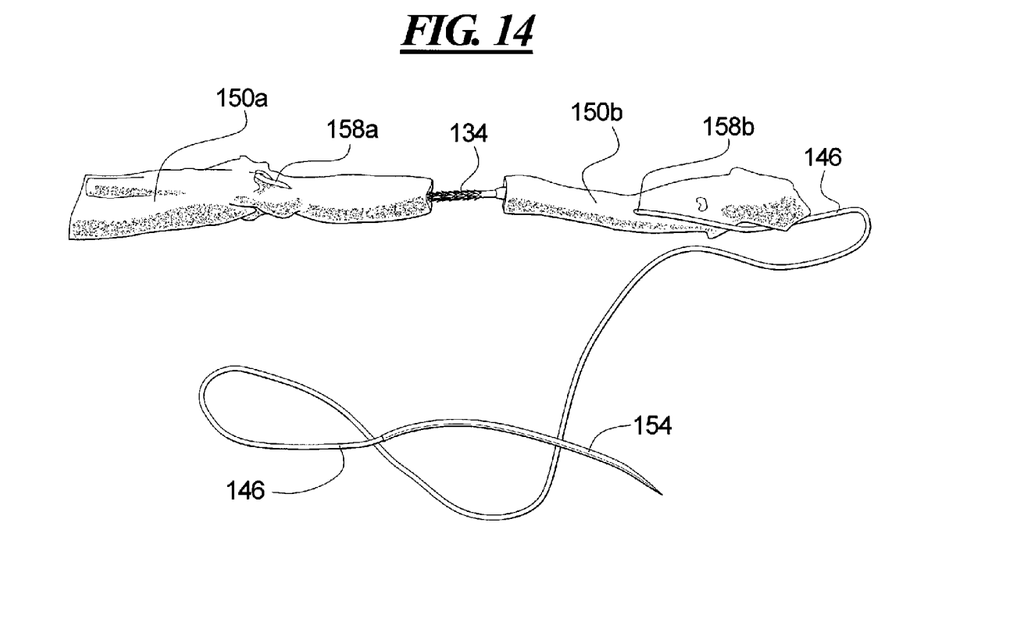
FIG. 14 is a photograph of the first preferred embodiment of the tendon repair apparatus with the suture being pulled into the second portion of the severed tendon.

Looking to FIG. 14, the suture 130 has been cut off at the exit location 158a on the first tendon portion 150a. The second needle 154 has been inserted into the second tendon portion 150b and drawn through to pull the second suture 146 through the tendon portion 150b up to the elongated member 134. The needle 154 is brought out of the second portion 150b at an exit location 158b. In FIG. 14, the elongated member 134 has not yet been pulled into the second portion 150b of the tendon.

Figure 15:
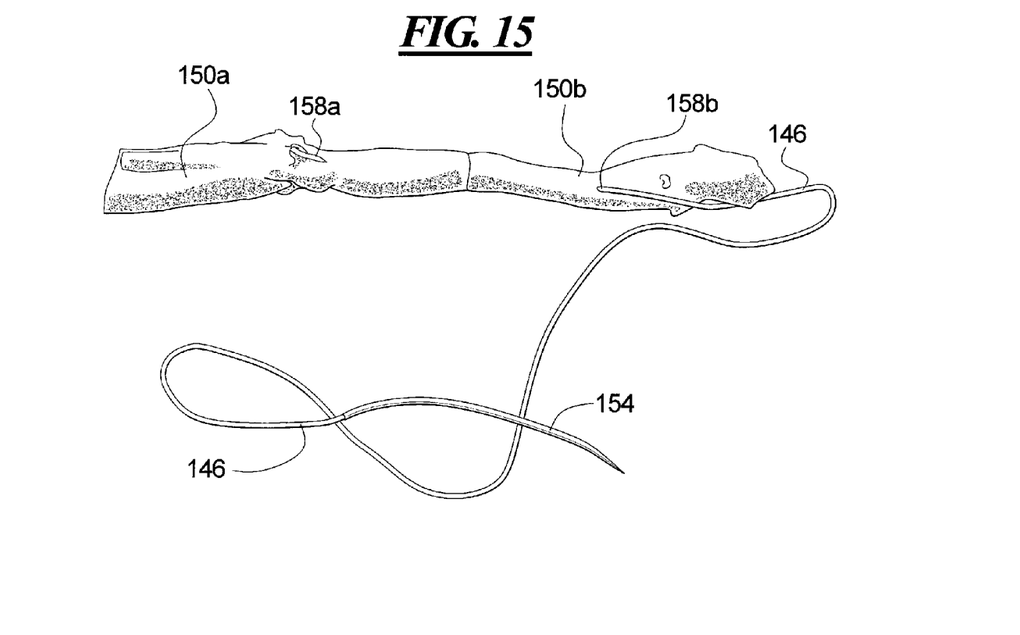
FIG. 15 is a photograph of the severed tendon after repair using the tendon repair apparatus of the first preferred embodiment and prior to one suture being cut off.

Turning to FIG. 15, the second suture 146 has been pulled further to draw the second barbed portion of the elongated member into the tendon. The tendon portions are now rejoined and will be held together by the barbed device that is extending through both portions and bridging the repair. The second suture 146 still extends from the second exit location 158b, but will cut off in the next step. Only two needle holes are made on the outside surface of the tendon, vastly reducing the number of sites for potential adhesion formation. Further, these needle holes are spaced a considerable distance from the repair site, thereby further reducing the chance of an adhesion or other healing complication.

Of note is that the tendon 150 has been repaired with a single tendon repair apparatus. Perimeter stitching, which can also be called circumferential suturing or peripheral suturing, may be used as desired by the medical professional, although in some instances no such stitching would be performed so that the tendon repair is now complete. Repair of the tendon is therefore a relatively simple and straightforward procedure.

Figure 16:
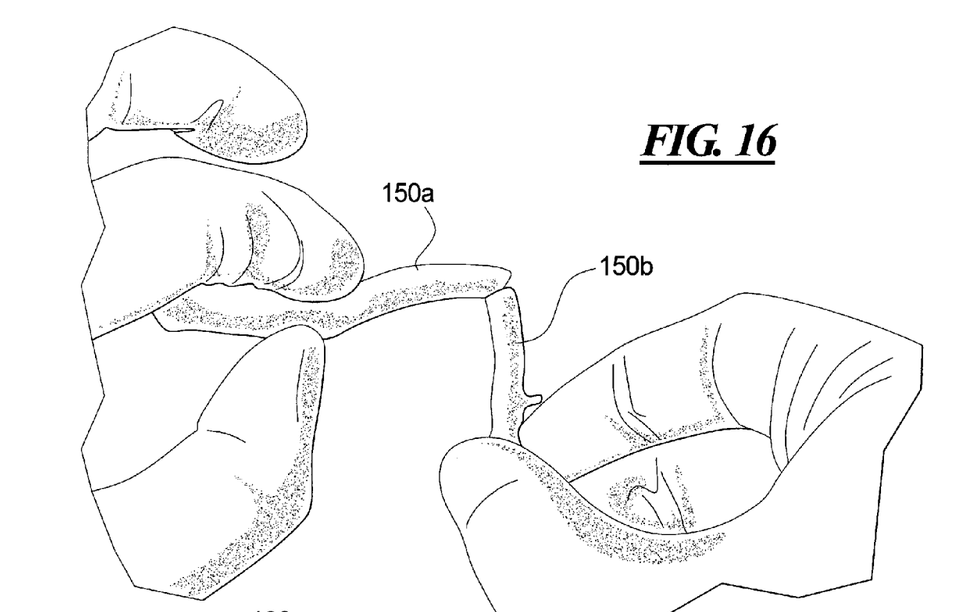
FIG. 16 is a photograph of the repaired tendon being flexed at the repair site.

In FIG. 16, the repaired tendon is shown being flexed at the repair location between the first and second portions 150a and 150b. The elongated portion 134 that is now inside the tendon and not visible in this view flexes at the middle portion so as to permit the tendon to be flexed but the barbed sections do not pull out. The material of the elongated member is not only flexible but returns to its original shape so that the tendon returns to its original condition after being released from the flexed position shown in FIG. 16.

Figure 17:
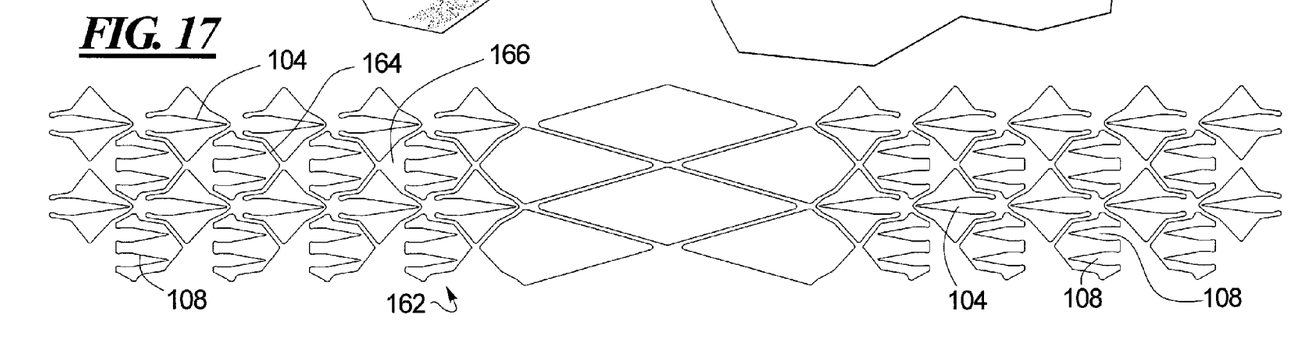
FIG. 17 is a schematic diagram of a vector cutting path for cutting a tube to form a tendon repair device according to a second preferred embodiment.

FIG. 17 shows a vector path 162 for a further preferred embodiment. The vector path 162 is used to cut a tube into an elongated member of the tendon repair device. The vector path 162 of FIG. 17 includes the long barbs 104 and the paired short barbs 108 in alternating columns supported by thin struts 164 and thick struts 166. The thin struts are adjacent the free ends of the paired smaller barbs 108 while the thick struts 166 are adjacent the base of the paired short barbs. The middle portion 114 is formed by elongated crossed struts 116. The embodiment of FIG. 17 is similar in most respects to the embodiment of FIG. 8.

Figure 18:
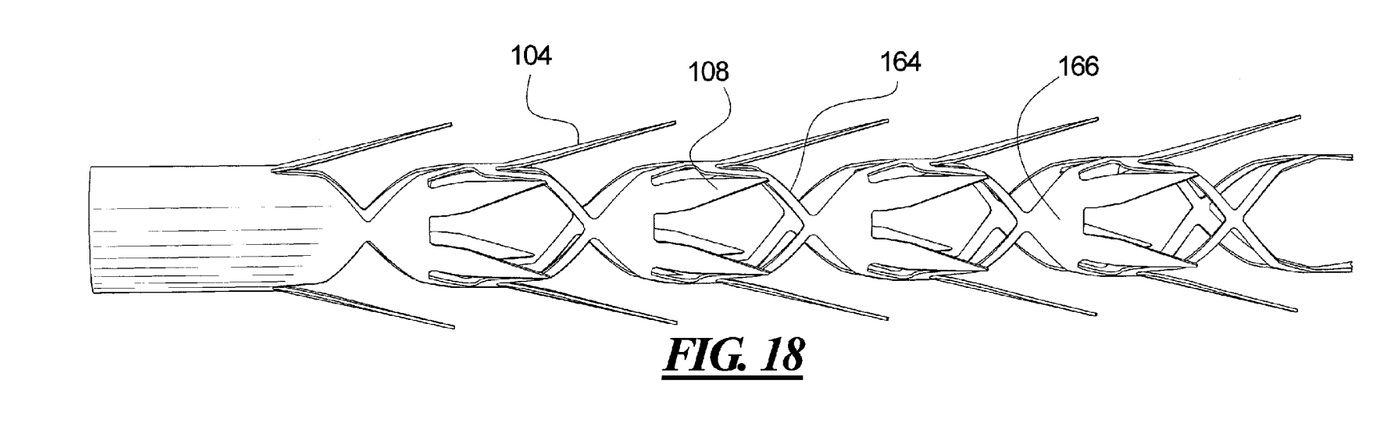
FIG. 18 is an enlarged photograph of a portion of the tendon repair device according to the second preferred embodiment.

In FIG. 18 is an enlarged view of the elongated device 134 formed by cutting a tube using according to the vector path of FIG. 17 and then bending the barbs 104 and 108 outward. The device has the large barbs 104 on opposite sides of the device and pairs of the shorter barbs 108 on the sides perpendicular to the large barbs. The device is thus asymmetrical as to rotational symmetry. This device may work best in tendons that have an elliptical or ellipsoidal cross section. As can be seen in this view, the struts 164 connecting the barbed section together can be quite thin, leading to a high stress applied to a small cross section of the material. Thicker material may be provided in some embodiments.

Since the device of one embodiment is formed by laser cutting of the metal tube, the laser has an affect on the metal adjacent the cutting path. The heat of laser cutting and subsequent cooling changes the characteristics of the metal along the edges of the cut in what is termed a heat affected zone. For instance, the crystal structure of the metal in the body of the tube prior to cutting typically results from a controlled annealing step. The heat affected zone has a changed micro structure adjacent the cut edges that can have a low tensile strength compared to the metal prior to cutting. If the laser cutting is carried out in cut lines that lie too close to one another, the heat affected zones may of the adjacent cuts may come close to one another, may contact one another or may even overlap. This has the effect of weakening the device. As such, a vector path may be chosen to keep the cutting paths from becoming too close to one another so that a greater cross section of unaffected material remains. A vector path may be chosen take into account the weakening of the heat affected zone so that less stress is placed on certain locations in the device. Another alternative is to change the material of which the device is made to a material that transmits heat less readily so that the head affected zone is narrowed. A further possibility is to perform the laser cutting in a way that the heat affected zone is less pronounced for example by pulsing the laser, or so that the strength of the heat affected zone is retained for example by performing an annealing step on the cut tube.

Figure 19:
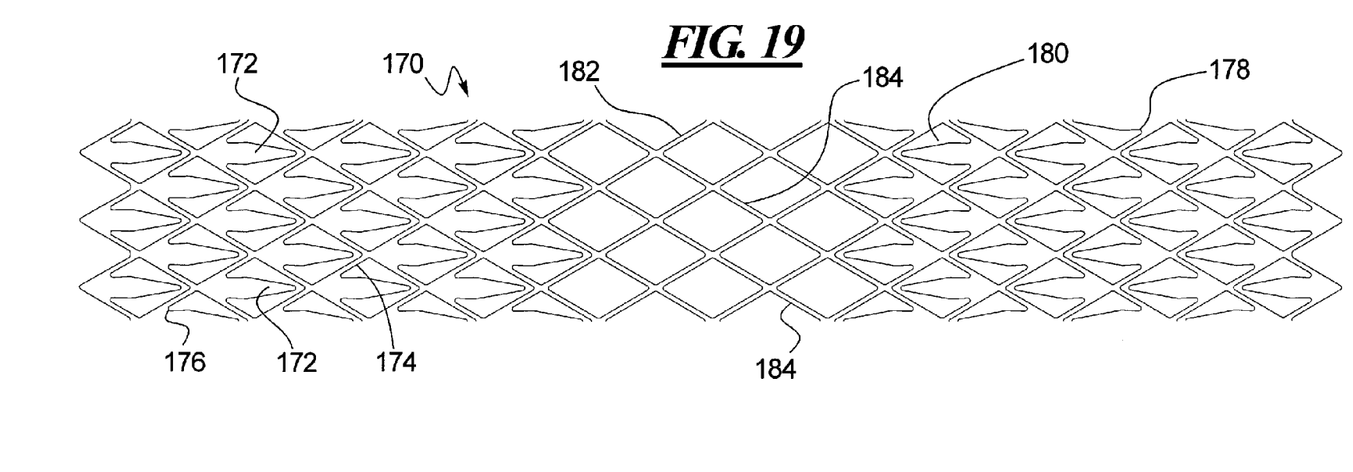
FIG. 19 is a schematic diagram of the vector cutting path for a tendon repair device according to a third preferred embodiment.

FIG. 19 is yet another vector path 170 for cutting a tube to form a different embodiment of the device. The barbs 172 are all uniform in size and shape in this embodiment as are the struts 174 that form the mesh body of the barbed portions 176 and 178. The device formed by this vector cutting path is rotationally symmetrical. The openings 180 are diamond shaped and in a regular arrangement so that the struts 174 are straight rather than curved. The middle portion 182 is formed of crossed struts 184 that are in the same arrangement as those of the barbed portions 176 and 178. The device resulting from cutting a tube with this vector path and bending the barbs outward has a generally circular cross section, as opposed to the elliptical cross section of the embodiment of FIG. 17.

Figures 20, 21, 22:
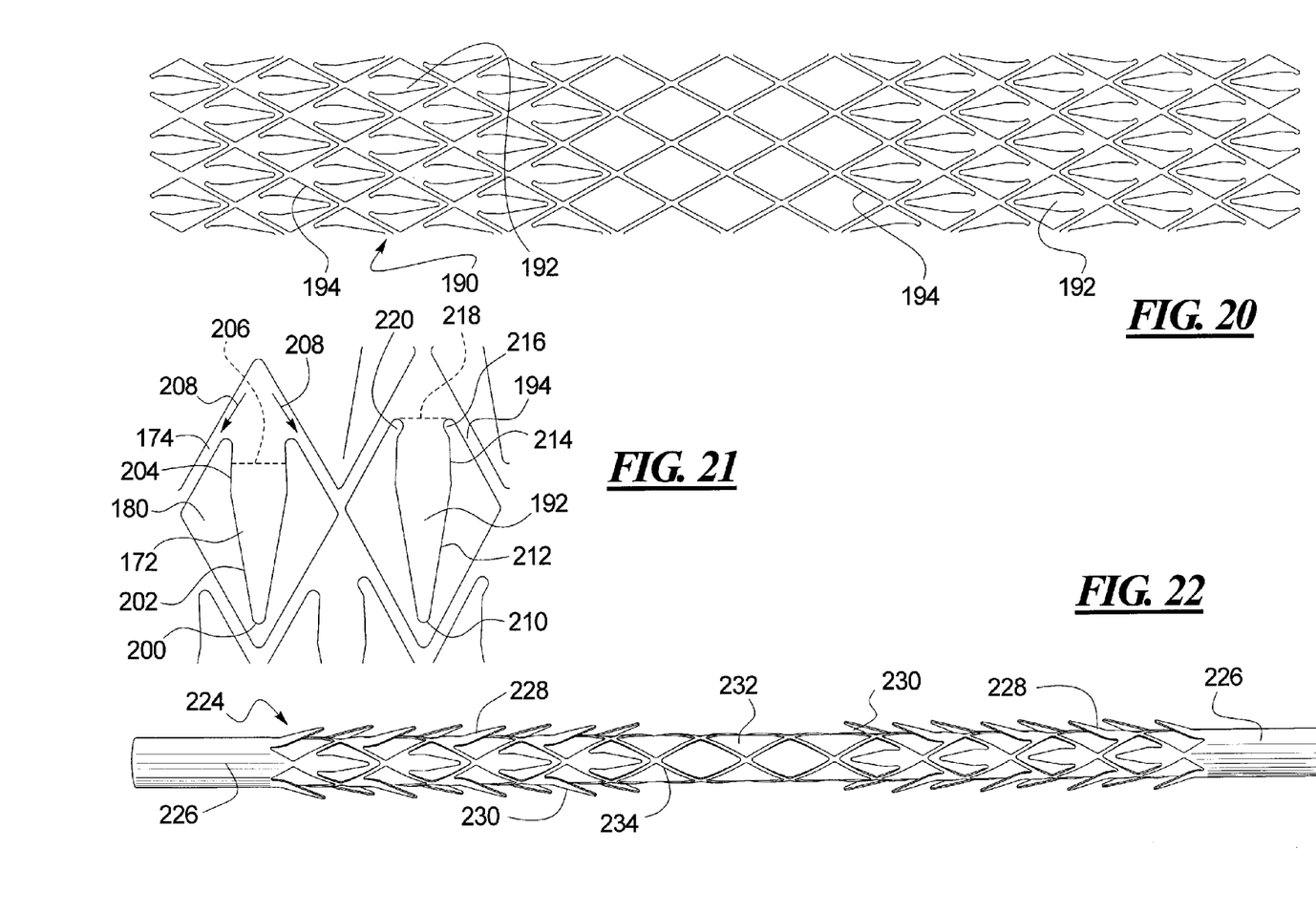
FIG. 20 is a schematic diagram of the vector cutting path for the tendon repair apparatus according to a fourth preferred embodiment.
FIG. 21 is an enlarged schematic diagram of the barbs of the third and fourth preferred embodiments in side-by-side comparison.
FIG. 22 is a further embodiment of the tendon repair apparatus having suture material extending through the middle portion of the device.

In a further development, FIG. 20 has yet a further vector 190 path for cutting a tube into a tendon repair apparatus. The barbs 192 are all uniform in size and shape but vary slightly from the embodiment of FIG. 19 by the shape at the base of the barb. In particular, the barbs 192 have a slight narrowing at the base where they connect to the struts 194. The narrowing permits bending of the barb 192 outward from the tubular body without putting as much stress on the struts 194. The vector path of FIG. 20 is in other respects like that of FIG. 19.

In FIG. 21 is an illustration of two the different barb configurations of the embodiments of FIGS. 19 and 20. In the configuration to the left half of FIG. 21, the barb 172 has a rounded end 200, tapered sides 202, and a straight base 204 that connects to the struts 174. The barb 172 is bent outward to form the biting element on the tendon repair device. Even bending of the barb 172 along the straight base 204, for example at the dashed line 206, results in stress at the struts 174 at locations indicated by arrows 208.

To the right side of FIG. 21, the barb 192 has a rounded tip 210, tapered sides 212, a straight shaft 214, and a narrowed base 216. The narrowed base 216 provides a bending location for bending the barb 192 outward with less stress on the struts 194. The bending of the barb 192 takes place at the dashed line 218. Since a smaller cross section of material is being bent, the bending forces required for bending the barbs from the tubular elongated member into the extended position is less. The narrowed base 216 is formed by cut in channels 220.

The barb 192 has a greater length, leading to a greater extension of the barb away from the tubular elongated body so thereby providing a greater engagement or bite of the barb into the tissue of the tendon. In some embodiments, a greater barb length is desired and the barb configuration to the right of FIG. 21 provides such greater barb length. When a pulling force is exerted on the elongated member, the barbs tend to flex outward, increasing in effective length. As such, forces tending to pull the two portions of the tendon apart result in the barbs biting more deeply into the tendon material to provide pull-out greater resistance.

FIG. 22 shows an embodiment of the tendon repair apparatus 224 that has the tube ends 226 from which extends the suture, barbed portions 228 having barbs 230, a middle portion 232 without barbs and formed only of struts, and a length of monofilament nylon or other material 234 that extends through at least a portion of the elongated member. The monofilament material 234 is preferably the suture material that is run all the way along the interior of the elongated member. Use of the monofilament suture material avoids problems with fraying of the braided polyester sutures during feeding of the suture through the device, although it may be possible to use braided suture material in some embodiments. The advantage of having suture material 234 in the device itself is that resistance to elongation of the device is improved, and therefore the gapping at the repair site in the repaired tendon is prevented. When subjected to load the device lengthens by collapsing of the middle portion 232. The diamond shaped openings of the middle portion in particular and to some extent the barbed portions 228 contract, leading to an overall increase in length of the device which occurs simultaneously with a decrease in diameter. This may be desirable in some embodiments but in others may be undesirable. By providing material 234 within the middle portion 232 the decrease in diameter is counteracted and therefore the amount of lengthening of the device is decreased.

The present tendon repair apparatus may be used to repair severed tendons by use of a single device for each repair, two devices for each repair, three or even four devices per repair. The device has sufficient strength to provide early mobilization without risk of rupture of the repaired tendon. The barbs bite into the tissue of the tendon sufficiently to hold the severed ends together and minimize gapping of the tendon. The lack of external sutures required by the present device minimizes external suture material and its associated roughness. The open mesh design of the device provides not only flexibility for flexion of the repaired tendon, but elasticity and space for vascularity in the repaired tendon. It is desirable in some embodiments of the device to use as little material as possible in the elongated member by forming thin struts and barbs for better flexibility, although other embodiments may use more material for durability and other qualities.

The material of the preferred elongated member is nitinol, although a device formed of a biodegradable material is also desired so as to permit resorbing of the device into the body. A polymer material may be molded into the shape of the elongated material rather than requiring cutting and bending of the barbs. The preferred material is a biodegradable polymer. Other cast, formed, molded or otherwise formed devices of many different materials are within the scope of the present invention. The hollow interior of the elongated member may be filled or partially filled at the core with a soft flexible biologically degradable or bio-resolvable polymer or other material. Other materials contemplated for inclusion in the core of the elongated member include stem cells, viral gene vectors, cytokines, growth hormones, biologically active agents, or polymers of different half lives to provide time dependent release of agents.

The flexing of the elongated member, both transversely and by elastic elongation permits the elongated member to act as a pump to pump biological or other agents into the tendon or even into the patient's body. For example angiogenesis can be promoted in the early stages of tendon healing with promotion of collagen formation in the fibroblastic and remodeling stages. The compression applied by the device on loading could further optimize the delivery of these factors, pumping out biologically active agents under the power of the patients own rehabilitation. As noted above, the device may also be coated. Such coatings, fillings or other materials may promote healing or treat other conditions in the patient.

The present device includes a plurality of openings formed in the elongated tubular member. The openings may be of any shape and arrangement. The preferred openings form a latticework or mesh. The latticework includes interconnected struts in a lattice arrangement. It is contemplated to provide a middle portion of the device without a latticework but instead with some other structure or material to provide flexibility in the middle portion. This flexible middle portion may be of a tube or rod or cable or bundle of flexible elements. It may be of the suture material, of the same material as the barbed portions or of a different material. The flexible middle portion facilitates mobilization of the tendon.

An alternative embodiment may lack the middle portion entirely, so that the barbed portions are adjacent one another without a barbless part therebetween.

Figure 23:
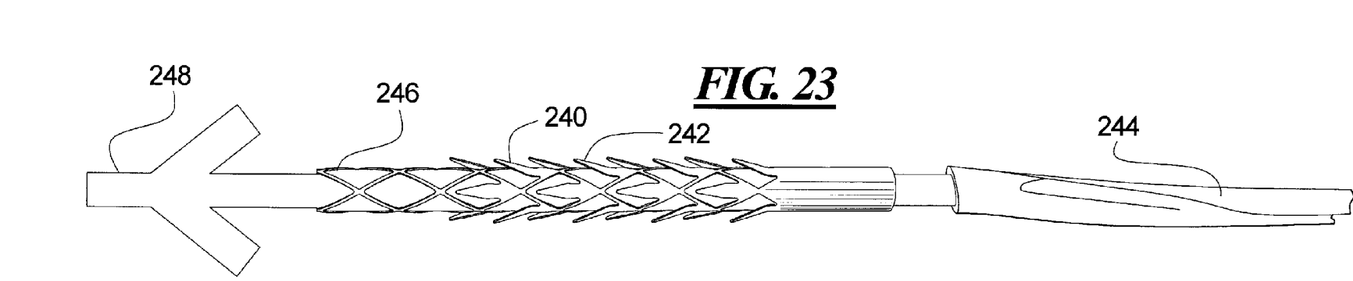
FIG. 23 is an illustration of a single ended device for attaching a tendon to a bone using a bone anchor.

As shown in FIG. 23, the elongated device 240 may be formed with only a single barbed portion 242 as a single ended device. The needle and suture 244 and barbed portion 242 of one end are provided as before, but the device ends approximately at the middle portion 246 of the foregoing devices, making a one ended device. The middle portion is replaced by or supplemented by a fastener or other attachment means 248 that permits that end to be attached to a bone or other body part. In the illustrated example, the attachment means 248 is a barbed bone-anchor type device. The bone anchor 248 is affixed to a bone while the barbed tendon repair device is inserted into the end of a tendon, so that the tendon is attached to the bone. Such a one ended device 240 may be used to attach a tendon that has ruptured at the bone or too close to the bone to use the two ended device shown in the foregoing.

Figure 24:
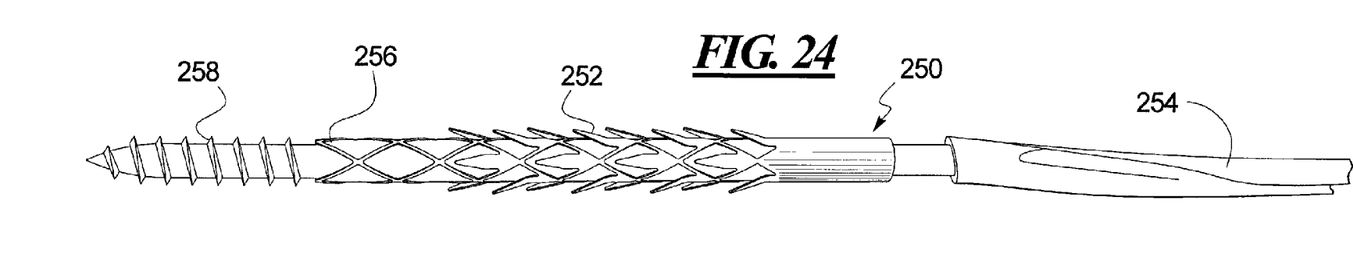
FIG. 24 is an illustration of a single ended device for attaching a tendon to a bone using a screw.

In FIG. 24, a tendon repair device 250 is provided with a single barbed section 252 and a suture 254, possibly connected to a needle. At what would be the middle portion 256 of a double ended device is connected a threaded screw 258 for connection to a bone so that the device 250 can be used to connect a tendon to a bone.

Figure 25:
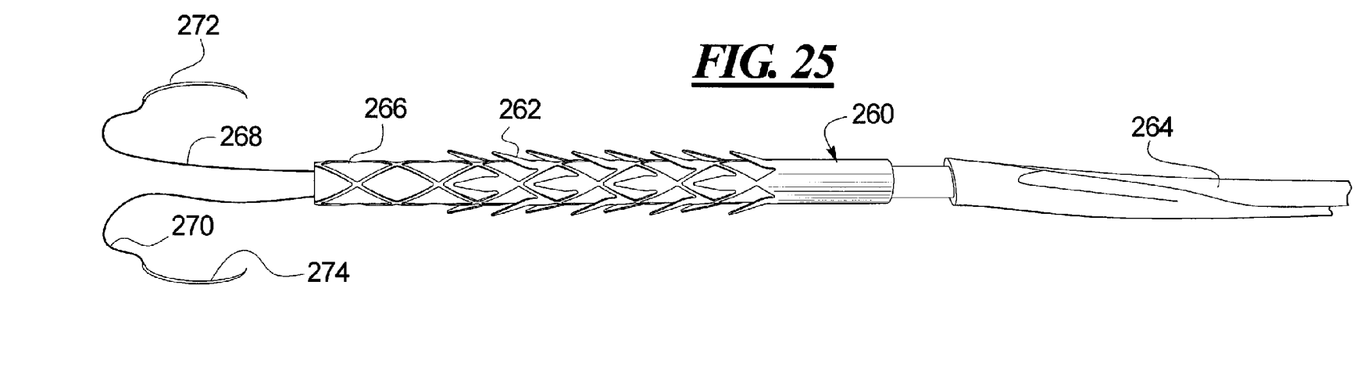
FIG. 25 is an illustration of a single ended device for attaching a tendon to a body element using a pair of sutures.

FIG. 25 shows yet another embodiment of a single ended tendon repair device 260. Like the others, it has a barbed section 262 and a suture 264. At what would be the middle portion 266 of a double ended device is connected a pair of sutures 268 and 270. Needles 272 and 274 are connected to the two sutures 268 and 270, respectively. The sutures 268 and 270 may be permanently connected or removably connected to the device 260. The two sutures 268 and 270 may be used to connect the device to a variety of body parts, including to bones. Other attachment methods or devices may be provided as well.

The foregoing represents only some examples of types of single and double ended tendon repair devices, sutures and fasteners that may be used within the scope of the present invention. The present invention encompasses mixing different elements of the illustrated embodiments into a new embodiment. For example, the two suture connector of FIG. 25 may be used on one or both ends of a double ended device having two barbed portions or at both ends of a single ended device.

The present device is preferably used for tendon repair but may also be used for repair of other connective tissues, such as ligaments. It is foreseeable to use such devices in repair of other body tissues, vessels or organs as well. The present device has particular utility for quick and efficient management of hand injuries, such as of the flexor tendon. Volar and dorsal tendons may be repaired with the present method and apparatus. The present device and method is far simpler than the four strand techniques of the prior art, which can still be relatively complex to perform, while creating repairs equivalent in strength to current four strand techniques.

Thus, the present method provides that a barbed device has a suture and needle attached to each end, these are introduced into the divided tendon and dragged through it. The device is pulled into the tendon by the suture and the excess is cut flush with the surface. The procedure is repeated with the other tendon end resulting in a completed repair. In some instances, two devices (or more) may be used for each repair in order to control rotation at the repair site and maximize the number of barbs in the tendon. It may be desirable in some cases to complete the repair with a peripheral stitch in order to leave a smooth tenorrhaphy and increase its strength, although this is not necessary in every instance.

The present method and device permits repair of a tendon with a smaller opening of the tendon sheath and other surrounding tissues, less handling of the tendon, and potentially less time required for the repair. Healing time and complications for the patient is thereby improved. More significantly, however, is the early mobilization of the tendon and effected limb that is possible using the present device and method. Accordingly, a minimally invasive tendon repair is provided.

Prototypes of the present device have been made and tested with good results. Its strength was equivalent to that of the two strand Pennington modified-Kessler repair of the prior art for all parameters except FPG (the force to produce a gap in the repaired tendon) when supplemented by a circumferential cross stitch. In this configuration the FPG of the device was equivalent to that of a cruciate four strand repair.

In conclusion, the device and method provide for minimal access flexor tendon repair. This device, on linear load to failure testing, has equivalent strength when used with a core repair to current four strand techniques. When two devices are used the repair is equivalent in strength to current six strand techniques.

Although other modifications and changes may be suggested by those skilled in the art, it is the intention of the inventors to embody within the patent warranted hereon all changes and modifications as reasonably and properly come within the scope of their contribution to the art.

We claim:

1. An apparatus for repair of a severed tendon having a first tendon portion and a second tendon portion to be rejoined, comprising:
   an elongated member of a substantially tubular shape and having a first end and a second end, said elongated member having a first barbed portion adjacent said first end and a second barbed portion adjacent said second end, said first and second barbed portions defining openings in said tubular member, said first barbed portion having barbs directed in an opposite direction relative to barbs of said second barbed portion,
   said elongated member having a tubular body of interconnected struts, wherein said barbs have a base connected to said tubular body of interconnected struts;
   a first suture connected to said first end of said elongated member;
   a first needle connected to said first suture at a position spaced from said elongated member;
   a second suture connected to said second end of said elongated member;
   a second needle connected to said second suture at a position spaced from said elongated member.

2. An apparatus as claimed in claim 1, wherein said elongated member includes a middle portion disposed between said first barbed portion and said second barbed portion, said middle portion being without barbs.

3. An apparatus as claimed in claim 1, wherein said first and second barbed portions each include a plurality of barbs extending at an angle from the tubular body of interconnected struts.

4. An apparatus as claimed in claim 3, wherein said plurality of barbs are of substantially equal length.

5. An apparatus as claimed in claim 3, wherein said plurality of barbs are of at least two different lengths.

6. An apparatus as claimed in claim 1, wherein said first and second barbed portions include a plurality of barbs, at least some of said barbs having a pointed free end, a taper extending from said pointed free end, and said base connected to said tubular body of interconnected struts.

7. An apparatus as claimed in claim 6, wherein said barbs have length and width, said barbs having a widest width at a portion spaced from said base so that said base is narrower than said widest width.

8. An apparatus for repair of a severed tendon having a first tendon portion and a second tendon portion to be rejoined, comprising:
   a tubular member of latticework defining a plurality of openings in said tubular member, said tubular member having first and second opposite ends, said tubular member being of a size and configuration to fit generally axially within the tendon to be rejoined;
   a plurality of barbs extending outward from said tubular member, said barbs defining first and second barbed portions wherein said barbs of said first barbed portion extend in an opposite directions with respect to said barbs of said second barbed portion, said first and second barbed portions defining openings in said tubular member, said first and second barbed portions being spaced from one another along a length of said tubular member, said barbs of each barbed portion being directed generally in a same direction relative to an axis of the elongated member to define a draw in direction for drawing the elongated member into a tendon, said barbs resisting withdrawal of the elongated member from the tendon in a direction opposite the draw in direction, wherein said barbs have a base connected to said tubular member of latticework;
   a first suture connection at said first opposite end of said tubular member, said first suture connection closing said first opposite end of said tubular member so as to permit said tubular member to be pulled into the tendon;
   a first suture connected at said first suture connection by which said tubular member is pulled into the tendon;
   a first needle connected to said first suture;
   a second suture connection at said second opposite end of said tubular member;
   a second suture connected to said second suture connection; and
   a second needle connected to said second suture.

9. An apparatus as claimed in claim 8, wherein said first and second barbed portions are formed of said latticework having said openings, said first and second barbed portions include at least one of said barbs connected to said latticework at each of said openings of said latticework in said first and second barbed portions.

10. An apparatus as claimed in claim 8, wherein said tubular member includes a middle portion between said first and second barbed portions, said middle portion being formed to be flexible.

11. An apparatus as claimed in claim 10, wherein said middle portion includes a latticework defining a plurality of openings in said middle portion of said tubular member.

12. An apparatus as claimed in claim 8, wherein said first and second suture are portions of a single length of suture material and said length of suture material extends through an interior space of said tubular member.

13. A tendon repair apparatus for repairing a severed tendon, comprising: an elongated tubular member having first and second opposite tubular ends, said elongated tubular member including a tubular body of interconnected struts;
   said tubular member having first and second barbed portions between said first and second opposite tubular ends, said first and second barbed portions defining openings in said tubular member;
   a plurality of barbs extending at an angle from said first and second barbed portions, said barbs of said first barbed portion being directed in an opposite direction relative to said barbs of said second barbed portion, wherein said barbs have a base connected to said tubular body of interconnected struts; and
   a middle portion between said first and second barbed portions, said middle portion being flexible,
   said first and second barbed portions and said barbs and said middle portion being of a same material.

14. A tendon repair apparatus as claimed in claim 13, further comprising:
   first and second sutures connected to said first and second opposite tubular ends of said elongated tubular member.

15. A tendon repair apparatus as claimed in claim 13, wherein said plurality of barbs each include a point, a tapered portion extending from said point, and said base connected to said elongated tubular member.

16. A tendon repair apparatus as claimed in claim 13. wherein said plurality of barbs are of substantially uniform size and shape.

17. A tendon repair apparatus as claimed in claim 13, wherein said plurality of barbs are of at least two different sizes.

18. A tendon repair apparatus as claimed in claim 13, wherein ones of said barbs are disposed in pairs in side-by-side arrangement.

19. A tendon repair apparatus as claimed in claim 13, wherein said openings in said tubular member form a latticework of interconnected struts.

* * * * *